US00PP09056P

United States Patent [19]

Pittman

[11] Patent Number: Plant 9,056

[45] Date of Patent: Feb. 14, 1995

[54] *RAPHIOLEPIS INDICA* VARIETY NAMED 'CONDA'

[75] Inventor: Jerry B. Pittman, Mobile, Ala.

[73] Assignee: Flowerwood Nursery Inc., Mobile, Ala.

[21] Appl. No.: 270,779

[22] Filed: Jul. 5, 1994

[51] Int. Cl.[6] ..... A01H 5/00

[52] U.S. Cl. ..... Plt./67.5

[58] Field of Search ..... Plt. 67.5

*Primary Examiner*—James R. Feyrer

[57] ABSTRACT

A new and distinct *Raphiolepis indica* plant which expresses a very high concentration of anthocyanin in new growth, has larger leaves and attains a larger ultimate size when compared with other commercial varieties in the market class. This plant is superior in development of a dense canopy of attractive coarse texture, with a high concentration of blossoms, but which produces no unwanted seed.

2 Drawing Sheets

BACKGROUND OF THE INVENTION

The new variety of *Raphiolepis indica* was found as an openly pollinated seedling of *Raphiolepis indica* 'Jack Evans', an unpatented variety, maintained in the Flowerwood Nursery at Dauphin Island Parkway, Mobile, Ala. The seedling was found in Apr., 1986. The new and distinct *Raphiolepis indica* plant of this invention comprises a novel and valuable Raphiolepis plant with a large branching structure, rapid growth rate, large coriaceous leaves, an abundance of pink flower clusters, and reddish-purple new growth. The new growth of this plant is interestingly and clearly red due to anthocyanin which is of distinctly higher concentration than in the parent variety. Unlike the parent plant, the plant of this invention, which has been named 'Conda', may be advantageously employed as a specimen appointment. The new variety has retained many of the outstanding attributes of its much smaller statured parent, in particular its tolerance of heat, drought, salt, insect, and disease which makes it adaptable to culture in most of the Sunbelt States. This plant is responsive to pruning and training and may be employed in forming dense, attractive hedges, and maintained without an excessive amount of care.

Having long internodes, this plant has a natural propensity to be a large plant and is thereby a valuable contribution to the industry for landscape uses which require a larger size plant. The upright habit of growth and the reddish new growth of this plant is similar to *Photinia*×*fraseri*, however, it is not as susceptible to fungal leaf spot.

Asexual propagation of the new plant by cuttings has been under Mr. Pittman's direction at the same location. The increased number or plants were evaluated and demonstrated stability of the new charateristics from generation to geenration. The plant cannot be reproduced true from seed.

SUMMARY OF THE INVENTION

The following are the most oustanding and distinquishing characteristics of the new cultivar when grown under normal horticultural practices in Mobile, Ala.

1. Fast growth rate under normal fertilization and moisture conditions.
2. Large form 10–12′ tall and 10–12′ wide.

3. Easily trained into a small tree.
4. Large leaves up to 7″ long have nice texture effect.
5. The Reddish/Purple color of the foliage is unique and offers a novel and strikingly appealing contrast of new foliage to old foliage in plants of this market class.
6. Flowers are Pink, fragrant, and very large.
7. Hardy to Zone 7.
8. Heat and drought tolerant.
9. Good plant for coastal areas because of wind and salt tolerance.
10. Has shown good resistance to leaf spot.
11. Very desirable in planters.
12. Makes a very good hedge or screen.
13. Produces no seeds and therefore will not result in the occurrence of unwanted seedlings or bird visitations.

DESCRIPTION OF THE DRAWINGS

This new variety of *Raphiolepis indica* is illustrated by the accompanying photographic prints in which.

Figure 1:
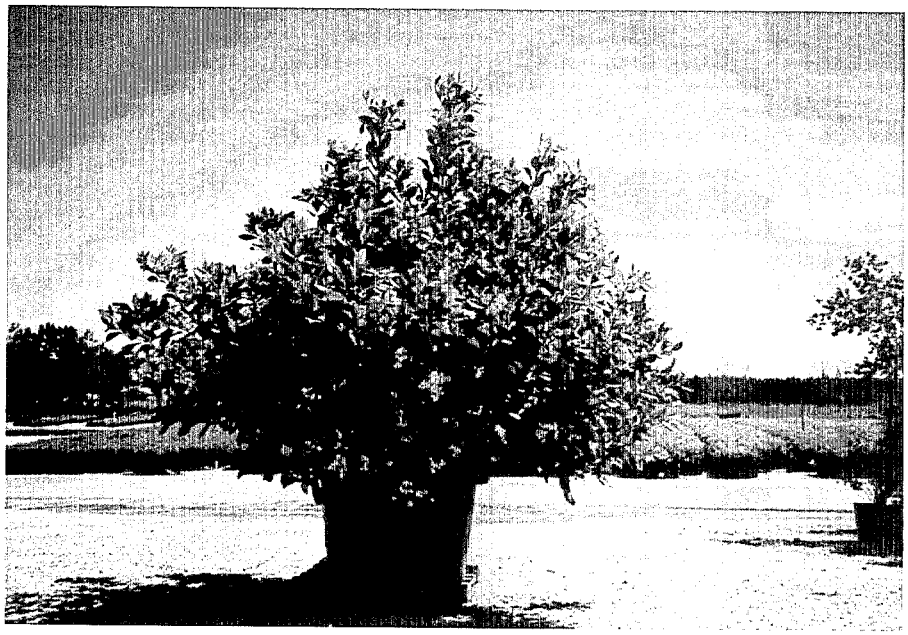
FIG. 1 discloses the large and upright nature of the new variety. It also shows the effective use and nature of use of the new variety as a hedge or screen.
Figure 2:
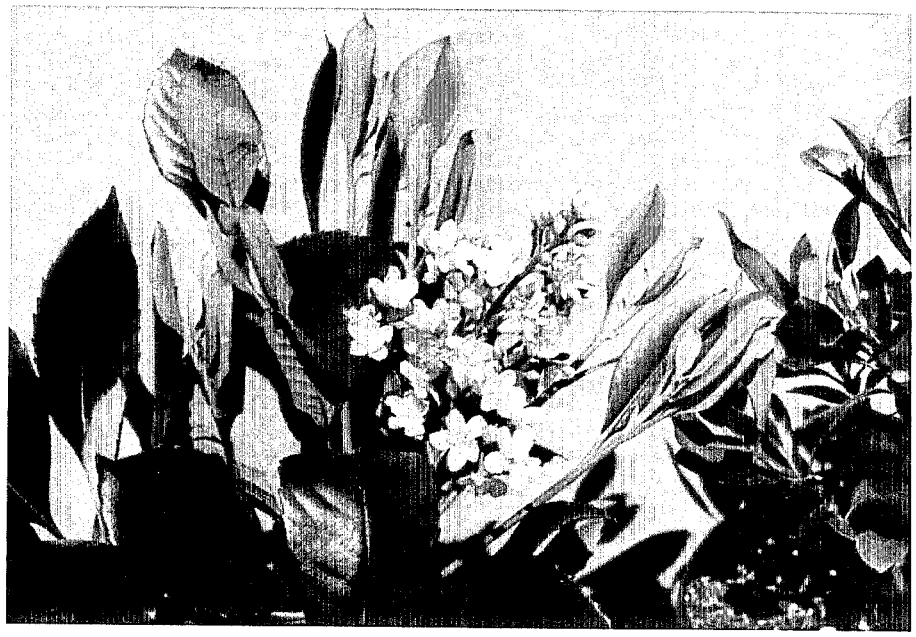
FIG. 2 shows a close-up view of a panicle of flowers and discloses the unusual reddish/purple pigmentation of the leaves, petioles, and stems of the juvenile growth. Also evident are the paired foliaceous stipules at the base of each petiole.
Figure 3:
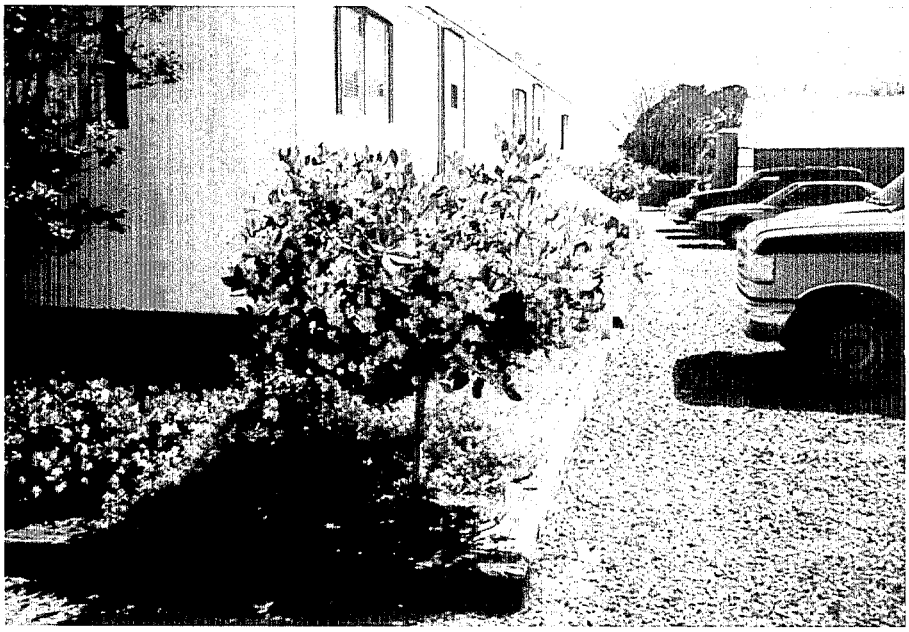
FIG. 3 shows the effective use and nature of use of the new variety as a small tree in an established landscape planting.
Figure 4:
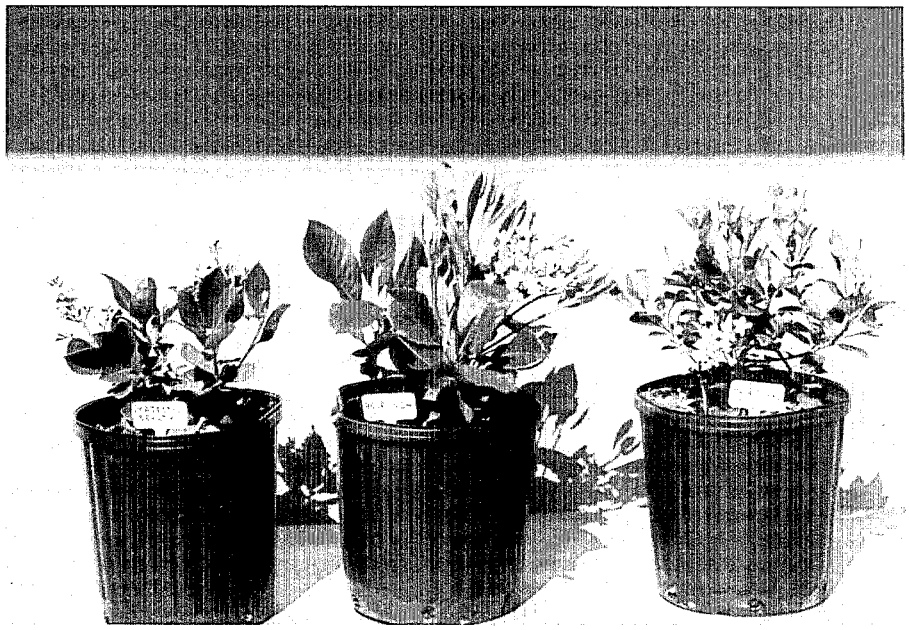
FIG. 4 is a side-by-side photograph of (from left to right) *Raphiolepis indica* 'Mantic' U.S. Plant Pat. No. 3,349, the new variety, and the parent of the new variety *Raphiolepis indica* 'Jack Evans'.

The colors shown are photographically as nearly true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Raphiolepis indica* based on my observations made of the plants grown in wholesale commercial production practices, in greenhouses, and established landscape plantings in Mobile, Ala.

| Distinctive Characteristics: Characteristic | 'Conda' | 'Jack Evans' | 'Montic' |
|---|---|---|---|
| Height (Mature) | 10–12 | 4–5' | 8–10' |
| Width (Mature) | 10–12' | 4' | 8–10' |
| Leaf Length | 6–7" | 2–3" | 5¾–6" |
| Leaf Width | 2½–3¼" | 1–1¼" | 2¼–2¾" |
| Foliage (New) | Greyed-Purple | Greyed-Orange | Greyed-Orange |
| Foliaceous Stipules | non-Caduclous | Caduclous | Caduclous |
| Petiole | ¾–⅞" | ½–¾" | ¾–⅞" |
| Flower | Pink/ Semi-double | Pink/Single | Pink/ Semi-double |
| Petals | 5–9 | 5 | 5–12 |
| Anthers | underdeveloped | Yellow | Yellow |
| Fruit | None | Black | Black |
| Growth Rate | Rapid | Slow | Moderate |

The Plant from which all above varieties originated has the botanical name Rosaceae *Raphiolepis indica.* The Author of the genus name Raphiolepis is John Lindley (1799–1865). The original author of the species name Indica is Carlolus Linnaeus (1707–1778) and the name was transfered to the plant *Raphiolepis indica* by John Lindley.

*Raphiolepis indica* 'Montic' U.S. Plant Pat. No. 3,349 was patented by Monrovia Nursery in 1973. It is comparable to the new plant in that both are larger growing than the species. However, there are many differences. The new plant has non-caducous paired stipules. It also has new foliage color Greyed-Purple 183A compared to Greyed-Orange 166A of 'Montic'. It has a larger mature leaf, larger overall plant size, and is a more vigorous grower. Both plants have semi-double perfect flowers, however, the anthers and stigma are underdeveloped in the new plant which prevents the plant from producing functional seed or pollen. The new plant has 5–9 petals Red-Purple Group 65A compared to 5–12 petals Red-Purple Group 62A.

It is from the seedlings of the *Raphiolepis indica* 'Jack Evans' plant that I found the new plant. This new variety will be sold under the trademark name Rosalinda. It will be listed *Raphiolepis indica* Rosalinda TM 'Conda'.

Classification:

*Botanic.—Raphiolepis indica* 'Conda'.

Form: Large, dense, upright and rounded.

Texture: Coarse, rather stiff in appearance.

Size: In a period of six years from a rooted cutting the plant reaches a height of 8 feet and a spread of 8 feet and has a 4 inch trunk caliper. The growth rate is normally about 16" or more per year ultimately reaching a height of 10 to 12 feet at maturity while maintaining a dense habit due to the abundant branch development.

Growth habit: Upright growing, dense and rounded evergreen shrub. Fast growth rate under normal fertilization and moisture conditions.

Foliage: Alternate, simple, evergreen, obovate to elliptic, and vary in size from 6–7" long and 2½31 –¼" wide. The margins are closely crenate to serrate, with a petiole ¾–⅞ long. The midrib is prominent on both sides of the leaf and the smaller veins are prominent on the underside. The base of the leaf is obtuse and the apex is broadly acute. The upper leaf surface of the mature leaf is Green Group 139A glossy and glabrous. The underside is Green Group 138B matte. The immature leaves are tomentulose, noticeably pigmented, and are Greyed-Purple Group 183A. The immature foliage in the winter is also Greyed-Purple Group 183A. The paired foliaceous stipules are ½–¾" long and ⅛–¼" wide. The upper surface is Green Group 141B and the underside is Yellow-Green Group 144A.

In 1992, the date of initial Spring growth was March 5, in Mobile, Ala. After the initial Spring flush there was almost continuous growth until Fall ending Oct. 22, also in Mobile, Ala. When grown in full sun, the internode length of this plant is ¾–½" compared to ½–¾" for the parent plant. When grown in light shade the internode length is 1–1¾". As would be expected either plant grown in shade results in a taller less dense plant with larger leaves.

The average length of terminal growth of the inital Spring flush is about 10" for a plant in full sun and about 12" when grown in shade. After this initial flush we normally trim the plant lightly and the plant then continues to grow about 6" until we trim it a second time in the early Fall. The Fall growth of about 6" then hides the cut limbs. We finish in the Fall with a three gallon plant about 30" tall and 28" wide. There is a striking difference between the vigor or this plant and the parent plant. Raphiolepis Jack Evans grown under identical conditions were only 15" tall and 14" wide at the end of the Fall.

Stems: The young shoots have a reddish pigmentation, Greyed-Purple Group 183A, and are tomentulose. The immature petioles, midribs, and veins are also Greyed-Purple Group 183A. After one or more years the stems are generally grey, Greyed-Green Group 197B, glabrous and rugose. The pith is solid and uniform. Young and older stems are brittle and densely branched. The stem's caliper increases quickly as the plant grows, which allows the plant to be easily trained as a patio tree.

Flowers: Perfect, however, the anthers and stigma are underdeveloped, semi-double, pin, Red-Purple Group 65A, ⅞" diameter, fragrant, born on dense, upright, tomentulose, 7–8" high and 5–6" wide terminal panicles from March to April. Each panicle has from 3–14 racemes which have from 3–16 flowers each, resulting in 100 or more flowers per panicle. A mature plant can have several hundred panicles. The flowers are attached to short pedicels which are ⅜–11/16" in length. The peduncle of each receme is from ¼–/4–4" long. Each flower has from 5 to 9 petals that are 5/16" wide and ⅜" long, and are lanciolate to obovate or spatulate in shape. The flower has from 15 to 20 stamen with underdeveloped anthers and one pistil consisting of three styles that are fused at the base or ovary and an underdeveloped stigma. There are five sepals which have ciliate margins. In 1992 the blooming period began March 14, in Mobile, Ala. and ended April 21.

Culture: Grows well in a wide range of conditions and tolerates sun to part shade. Grows in nearly any soil type, from moist to very dry and sand to clay. Responds well to mulching and medium applications of fertilizer; prefers ph 6 to 7. Very little pruning is needed. Can be pruned-up unto a small tree; adaptable to containers and above ground planters; strong charater results in good informal hedge with excellent foliage and flower contrast. Ideal for coastal regions and warmer parts of Piedmont. Tolerates wind and salt spray. Propagated with semi-hardwood cuttings in late Spring thru the summer.

Pests: Leaf spot can be a problem in moist shady locations but is less of a problem to this new variety than the parent.

I claim:

1. A new and unique variety of *Raphiolepis indica* plant named *Raphiolepis indica* 'Conda' as herein shown and described, is characterized by its large branching structure, rapid growth rate, very large coriaceous leaves, abundance of large clusters of pink flowers, and reddish-purple new-growth; the increased stature and vigor will fill numerous landscape needs for large screens, hedges, specimen plants and unusual foliage coloration and for its tolerance of heat, drought, salt, insects, disease, and soil type.

* * * * *